(12) United States Patent
Lockwood

(10) Patent No.: US 8,267,147 B2
(45) Date of Patent: Sep. 18, 2012

(54) DENTAL SHIELD APPARATUS

(76) Inventor: Robin R. Lockwood, Oklahoma City, OK (US)

( * ) Notice: Subject to any disclaimer, the term of this patent is extended or adjusted under 35 U.S.C. 154(b) by 197 days.

(21) Appl. No.: 12/821,573

(22) Filed: Jun. 23, 2010

(65) Prior Publication Data

US 2011/0318702 A1    Dec. 29, 2011

(51) Int. Cl.
*A47G 1/00* (2006.01)
(52) U.S. Cl. .............. 160/351; 433/29; 248/104
(58) Field of Classification Search .......... 160/351; 128/849; 451/455; 362/220, 222; 248/104, 248/276.1, 160, 219.4, 229.12, 228.3, 231.85, 248/218.4, 231.71, 214, 229.15; 349/14; 313/48; 433/29
See application file for complete search history.

(56) References Cited

U.S. PATENT DOCUMENTS

| | | | | |
|---|---|---|---|---|
| 354,976 A * | 12/1886 | Field | ............................ | 248/484 |
| 1,470,774 A * | 10/1923 | Spence | ......................... | 248/160 |
| 1,580,903 A * | 4/1926 | Kelleher | ....................... | 451/455 |
| 1,633,412 A * | 6/1927 | Kelleher | ....................... | 451/455 |
| 2,041,847 A * | 5/1936 | Marchand | ..................... | 248/160 |
| 2,712,039 A * | 6/1955 | Holmes | .......................... | 379/455 |
| 2,994,501 A * | 8/1961 | Barnard | .................. | 248/231.61 |
| D216,414 S * | 12/1969 | Hanson | ......................... | D6/308 |
| 4,934,766 A | 6/1990 | Schmidt et al. | | |
| 5,012,852 A | 5/1991 | Blackhurst | | |
| 5,398,176 A * | 3/1995 | Ahuja | ........................... | 362/253 |
| 5,699,988 A * | 12/1997 | Boettger et al. | ........... | 248/122.1 |
| 5,865,182 A * | 2/1999 | Chen | ............................. | 128/846 |
| 6,155,823 A * | 12/2000 | Nagel | ............................ | 433/29 |
| 2011/0318702 A1 * | 12/2011 | Lockwood | ...................... | 433/50 |

\* cited by examiner

*Primary Examiner* — Blair M. Johnson
(74) *Attorney, Agent, or Firm* — Dale J. Ream

(57) ABSTRACT

A dental shield apparatus includes a first portion of flexible tubing having proximal and distal ends. A handle is operably coupled to the distal end of the first portion of flexible tubing. The dental shield apparatus includes a transparent shield. Second and third portions of flexible tubing operatively couple the transparent shield to the handle, the second portion of flexible tubing having a mass per unit length that is less than a mass per unit length of the first portion of flexible tubing. The third portion of flexible tubing includes a mass per unit length that is less than the mass per unit length of the first portion of flexible tubing. The proximal end of the first portion of flexible tubing is attached to an anchor.

15 Claims, 4 Drawing Sheets

DENTAL SHIELD APPARATUS

BACKGROUND OF THE INVENTION

This invention relates generally to shielding devices and, more particularly, to a dental shield apparatus for shielding oral health providers from oral fluids, tooth particles, and blood that may be ejected at high velocities from a patient's mouth during dental procedures.

Modern dental devices operate at very high velocities and various types of waste particles may be ejected during a dental procedure. For example, some dental tools may operate at over five hundred thousand rotations per minute (rpm). As in the mechanical trades appropriate protective devices must be utilized when using these high rpm dental tools to prevent injury.

Various devices have been proposed in the art for shielding healthcare workers, including dental personnel. Although assumably effective for their intended purposes, the existing protective shielding devices are either ineffective to adequately shield a dental health provider or are not used as frequently as needed because they are not easily positionable where needed.

Therefore, it would be desirable to have a dental shield apparatus that is substantially transparent, durable, and adjustable to virtually any position without significant effort. Further, it would be desirable to have a dental shield that may be attached to a dental chair and provides lighting options.

SUMMARY OF THE INVENTION

A dental shield apparatus according to the present invention includes a first portion of flexible tubing having proximal and distal ends. A handle is operably coupled to the distal end of the first portion of flexible tubing. The apparatus includes a transparent shield. Second and third portions of flexible tubing operatively couple the transparent shield to the handle, the second portion of flexible tubing having a mass per unit length that is less than a mass per unit length of the first portion of flexible tubing. The third portion of flexible tubing includes a mass per unit length that is less than the mass per unit length of the first portion of flexible tubing. The proximal end of the first portion of flexible tubing is attached to an anchor such as a dental chair.

Therefore, a general object of this invention is to provide a dental shield apparatus for shielding a dental health provider from ejection of oral fluids and particles generated during an oral procedure.

Another object of this invention is to provide a dental shield apparatus, as aforesaid, that includes a shatterproof shield.

Still another object of this invention is to provide a dental shield apparatus, as aforesaid, that includes flexible tubing that is adjustable in multiple directions.

Yet another object of this invention is to provide a dental shield apparatus, as aforesaid, that may be attached to a dental chair.

A further object of this invention is to provide a dental shield apparatus, as aforesaid, that includes a light.

Other objects and advantages of the present invention will become apparent from the following description taken in connection with the accompanying drawings, wherein is set forth by way of illustration and example, embodiments of this invention.

DESCRIPTION OF THE PREFERRED EMBODIMENT

Dental shield apparatus according to the present invention will now be described in detail with reference to FIGS. 1 through 4*c* of the accompanying drawings. More particularly, a dental shield apparatus 100 according to one embodiment includes first, second, and third portions of flexible tubing 110, 120, 130, a handle 140, and a transparent shield 150.

Figure 1:
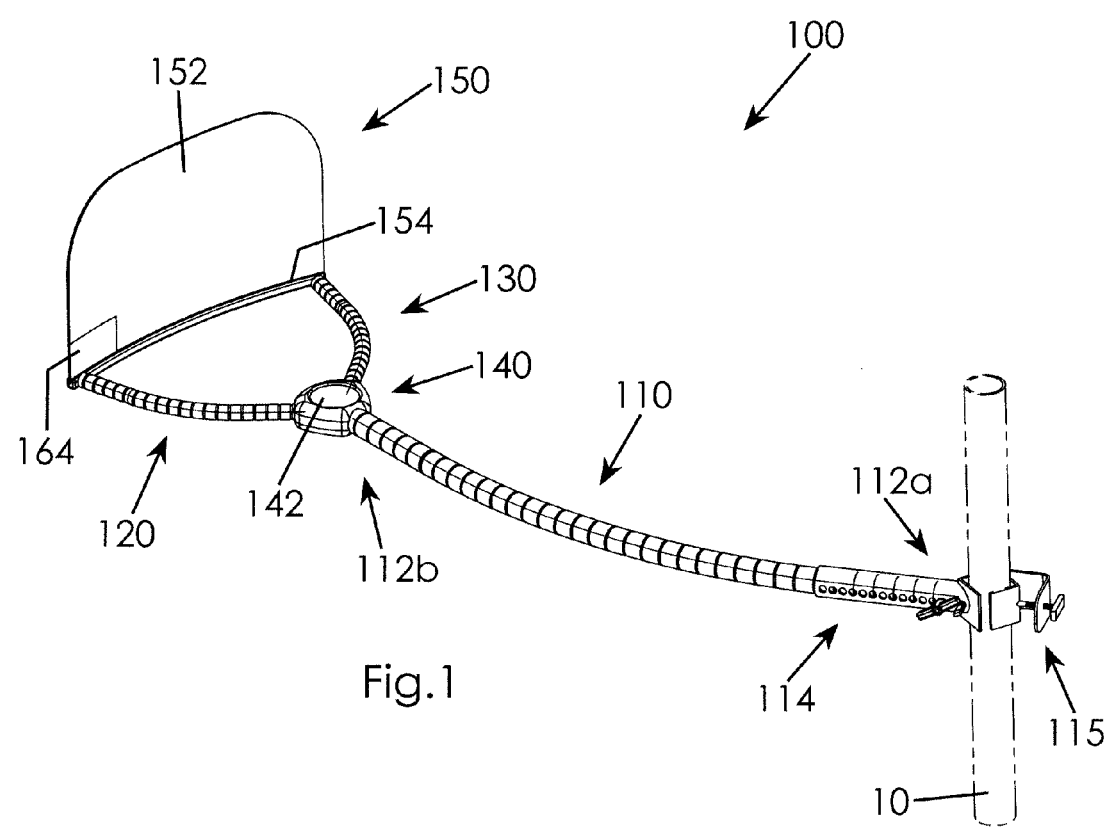
FIG. 1 is a perspective view of a dental shield apparatus according to a preferred embodiment of the present invention.
Figure 2:
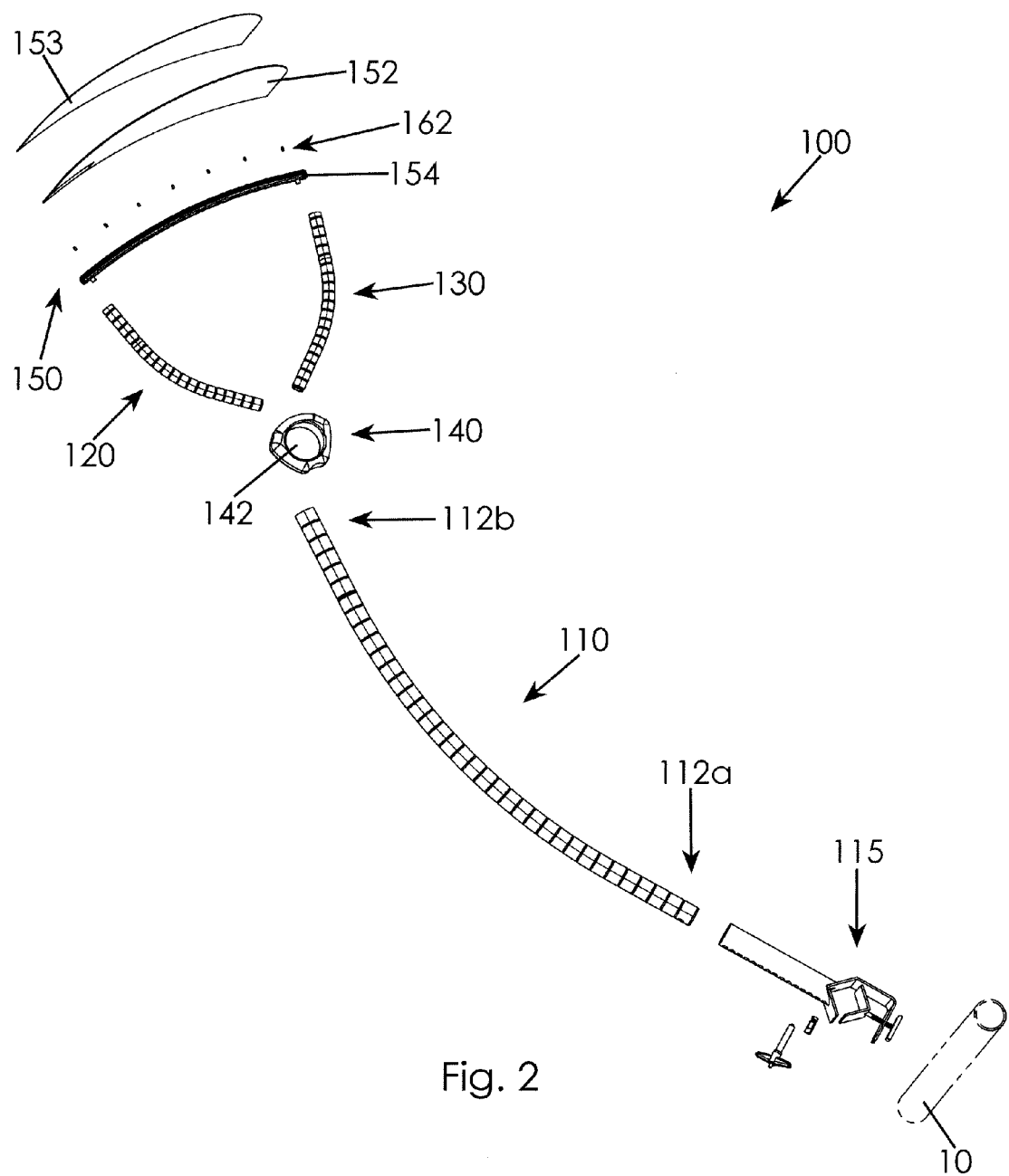
FIG. 2 is an exploded view of the dental shield apparatus as in FIG. 1.

As shown in FIGS. 1 and 2, the first portion of flexible tubing 110 has a proximal end 112*a* and a distal end 112*b* operatively coupled to the handle 140. A telescopic area 114 may be included (e.g., at proximal end 112*a*) for adjusting a length of the first portion of flexible tubing 110, and the first portion of flexible tubing 110 may be hollow and primarily constructed of stainless steel flexible tubing or other appropriate material that may maintain its configuration when repeatedly readjusted.

Figure 3:
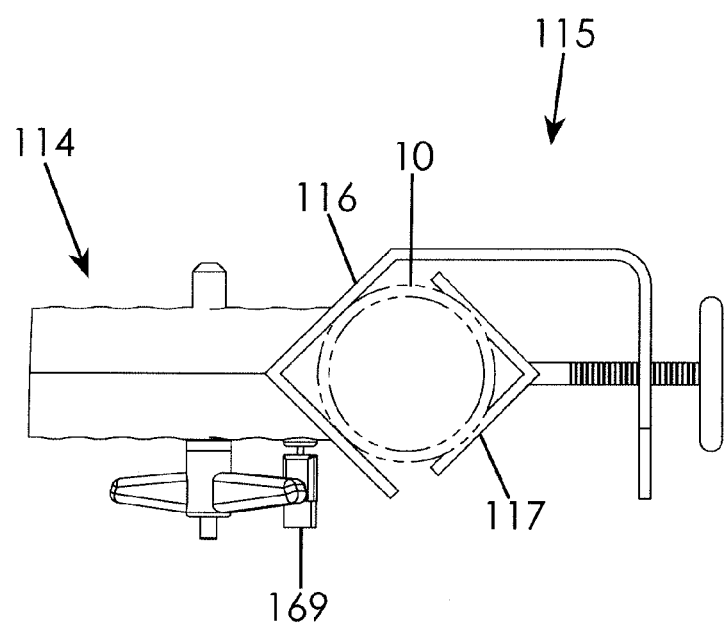
FIG. 3 is a top view of the fastener as in FIG. 1 attached to an anchor such as a dental chair.

A fastener 115 (FIGS. 1 through 3) may be included for operatively coupling the proximal end 112*a* to an anchor 10, such as a portion of a dental chair. The fastener 115 may, for example, include a base 116 and a clamp 117 movable relative to the base 116. The base 116 and the clamp 117 are shown in FIG. 3 to have opposed v-shaped cross sections for receiving anchors 10 having rectangular and rounded cross sections.

The second and third portions of flexible tubing 120, 130 (FIGS. 1 and 2) each operatively couple the transparent shield 150 to the handle 140. As with the first portion of flexible tubing 110, the second and third portions of flexible tubing 120, 130 may be hollow and primarily constructed of stainless steel flexible tubing or other appropriate material that may maintain its configuration when repeatedly readjusted. It may be very desirable for the second and third portions of flexible tubing 120, 130 to each have a mass per unit length that is less than a mass per unit length of the first portion of flexible tubing 110. This may be accomplished, for example, by the first portion of flexible tubing 110 being a heavier gauge of material than the second and third portions of flexible tubing 120, 130, by using different types of material for the different portions, or by using different diameters of material for the different portions. FIGS. 1 and 2 show the first portion of flexible tubing 110 having a diameter that is greater than a diameter of the second portion of flexible tubing 120 and that is greater than a diameter of the third portion of flexible tubing 130.

Turning to the handle 140 (FIGS. 1 and 2), the handle 140 may be hollow, and a hole 142 may additionally extend through the handle 140. It may be preferable for the hole 142 to have a diameter that is greater than the diameter of the first portion of flexible tubing 110, and for the handle 140 to be constructed of a relatively light-weight material. As shown, the distal end 112*b* of the first portion of flexible tubing 110 may be operatively coupled to one side of the handle 140, and the second and third portions of flexible tubing 120, 130 may be operatively coupled to (and spaced about) an opposite side of the handle 140.

Attention is now directed to the transparent shield 150 (FIGS. 1, 2, 4a, 4b, and 4c). The transparent shield has a transparent portion 152, which may for example be arcuate. A film 153 may be removably coupled to the transparent portion 152 for protecting the transparent portion 152 and/or for sanitary purposes. A base 154 may also be included, and the transparent shield may be removably coupled to the base 154 (e.g., by screws or other fasteners). The base 154 may have a channel 155 for receiving the transparent portion 152, and may include mounting structure 156 (FIGS. 4a and 4c) for coupling the second and third portions of flexible tubing 120, 130 to the transparent shield 150.

Figure 4A:
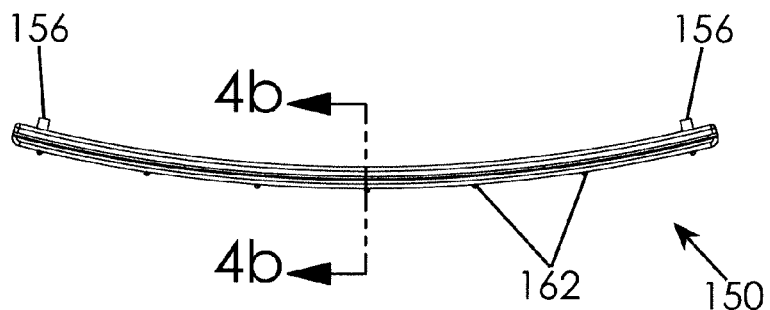
FIG. 4*a* is a top view of the shield as in FIG. 1.
Figure 4B:
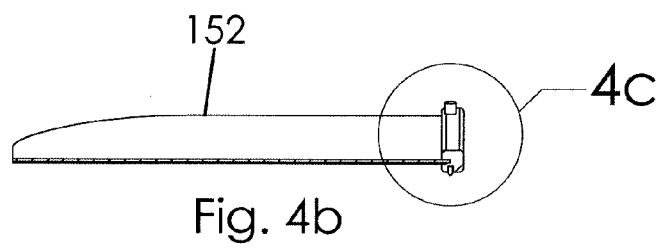
FIG. 4*b* is a sectional view taken along line 4*b*-4*b* of FIG. 4*a*.
Figure 4C:
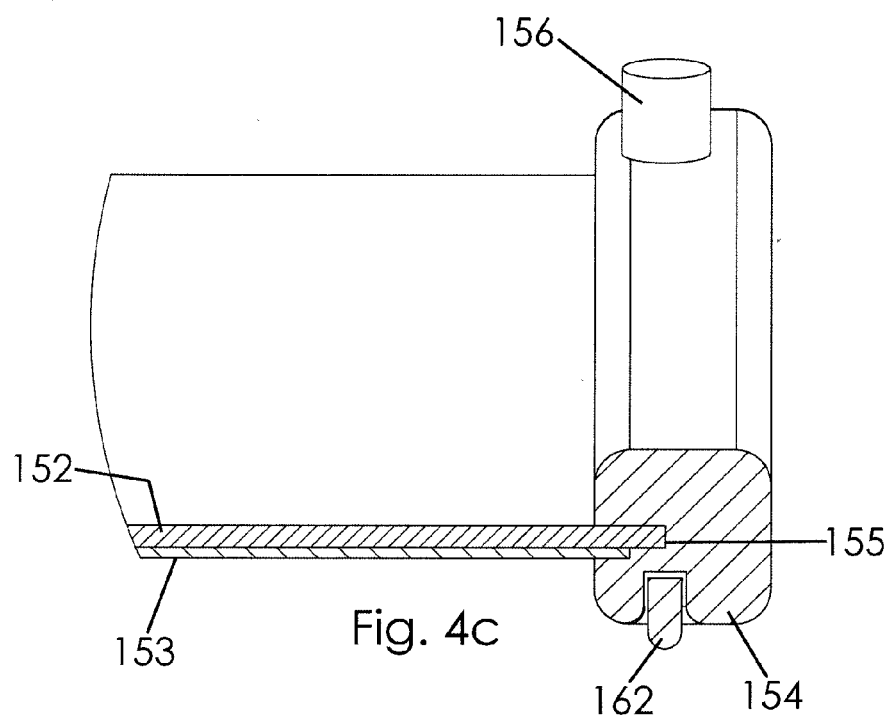
FIG. 4*c* is an isolated view on an enlarged scale taken from a portion of FIG. 4*b*.

It may be desirable for the transparent shield 150 to include at least one electrical device, such as a light 162 or a display 164, and wiring may extend from the electrical device through the second and/or third portions of flexible tubing 120, 130, the handle 140, and the first portion of flexible tubing 110. FIG. 4c shows one light 162 (e.g., a LED) coupled to the base 154, and FIG. 1 shows one display 164 located in a corner of the transparent shield 150. The display 164 shown in FIG. 1 may be viewable on one side of the transparent shield 150 or the other. In other embodiments, a transparent display may be included along all or part of the transparent portion 152. Such a transparent image may be provided by a projector or other appropriate technology, as will be appreciated by those skilled in the art.

In use, the fastener 115 may couple the proximal end 112a of the first portion of flexible tubing 110 to an anchor, such as a portion of a dental chair. A user may grab the handle 140 (e.g., by placing one or more finger inside the hole 142) and manipulate the positioning of the distal end 112b of the first portion of flexible tubing 110. To lengthen or shorten the first portion of flexible tubing 110, the telescopic area 114 may be adjusted. The positioning of the transparent shield 150 may be further manipulated by moving and adjusting the second and third portions of flexible tubing 120, 130, which may be accomplished by simply gripping and moving the transparent shield 150. Ultimately, the transparent shield 150 may be positioned such that the transparent shield 150 is between a patient and a medical provider (e.g., a dentist or hygienist). The disclosed configurations may minimize torque on the first portion of flexible tubing 110, allowing various positioning to be achieved and maintained.

The transparent portion 152 may catch flying debris (e.g., particles that become airborne from a dental procedure), and removing the film 153 may allow the received debris to be discarded. The electrical device may, for example, aid in lighting a work area, entertain the patient, provide the medical provider information about the patient, and/or aid in completing a medical procedure. If a transparent display is included, information or images (either static or dynamic) may in effect overlay the work area to aid the medical provider. The electrical device may receive data from a computer or other device through the wiring described above, and a data coupling device 169 (FIG. 3) may extend from the wiring for receiving data.

It is understood that while certain forms of this invention have been illustrated and described, it is not limited thereto except insofar as such limitations are included in the following claims and allowable functional equivalents thereof.

The invention claimed is:

1. A dental shield apparatus, comprising:
    a first portion of flexible tubing having proximal and distal ends;
    a handle operably coupled to said distal end of said first portion of flexible tubing;
    a transparent shield;
    second and third portions of flexible tubing each operatively coupling said transparent shield to said handle, said second portion of flexible tubing having a mass per unit length that is less than a mass per unit length of said first portion of flexible tubing, said third portion of flexible tubing having a mass per unit length that is less than said mass per unit length of said first portion of flexible tubing;
    means for attaching said proximal end of said first portion of flexible tubing to an anchor;
    wherein:
        said first, second, and third portions of flexible tubing comprise stainless steel flexible tubing;
        said first portion of flexible tubing has a diameter that is greater than a diameter of said second portion of flexible tubing;
        said diameter of said first portion of flexible tubing is greater than a diameter of said third portion of flexible tubing;
        a hole extends through said handle, said hole having a diameter that is greater than said diameter of said first portion of flexible tubing;
        said transparent shield has a base and an arcuate transparent portion removably coupled to said base; and
        said second and third portions of flexible tubing are each coupled to said base.

2. The dental shield of claim 1, wherein said first portion of flexible tubing includes a telescopic area for adjusting a length of said first portion of flexible tubing.

3. The dental shield of claim 2, further comprising a film removably coupled to said arcuate transparent portion for protecting said arcuate transparent portion.

4. The dental shield of claim 3, wherein:
    said transparent shield includes an electrical device; and
    wiring extends from said electrical device through: (a) at least one of said second and third portions of flexible tubing, (b) said handle, and (c) said first portion of flexible tubing.

5. The dental shield of claim 4, wherein said electrical device is selected from the group consisting of a light and a display.

6. The dental shield of claim 4, wherein said electrical device is a display located in a corner of said transparent shield.

7. The dental shield of claim 4, wherein said electrical device is a transparent display.

8. The dental shield of claim 1, wherein:
    said transparent shield includes an electrical device; and
    wiring extends from said electrical device through: (a) at least one of said second and third portions of flexible tubing, (b) said handle, and (c) said first portion of flexible tubing.

9. The dental shield of claim 8, wherein said electrical device is selected from the group consisting of a light and a display.

10. The dental shield of claim 1, wherein a hole extends through said handle, said hole having a diameter that is greater than a diameter of said first portion of flexible tubing.

11. The dental shield apparatus of claim 1, wherein said means for attaching includes a base and a clamp having opposed v-shaped cross sections for receiving anchors having rectangular and rounded cross sections, said clamp being movable relative to said base.

12. The dental shield apparatus of claim 1, wherein said transparent shield includes an electrical device selected from the group consisting of a light and a display.

13. A dental shield apparatus, comprising:
- a first portion of flexible tubing having proximal and distal ends;
- a handle operably coupled to said distal end of said first portion of flexible tubing;
- a transparent shield;
- second and third portions of flexible tubing each operatively coupling said transparent shield to said handle, said second portion of flexible tubing having a diameter that is less than a diameter of said first portion of flexible tubing, said third portion of flexible tubing having a diameter that is less than said diameter of said first portion of flexible tubing;
- a fastener for attaching said proximal end of said first portion of flexible tubing to an anchor;

wherein:
- said transparent shield includes an electrical device; and
- wiring extends from said electrical device through: (a) at least one of said second and third portions of flexible tubing, (b) said handle, and (c) said first portion of flexible tubing.

14. The dental shield apparatus of claim 13, wherein a hole extends through said handle, said hole having a diameter that is greater than said diameter of said first portion of flexible tubing.

15. The dental shield apparatus of claim 13, wherein said transparent shield includes an electrical device selected from the group consisting of a light and a display.

\* \* \* \* \*